(12) United States Patent
Sugimoto

(10) Patent No.: US 6,374,199 B1
(45) Date of Patent: Apr. 16, 2002

(54) INSPECTION AND ANALYZING APPARATUS FOR SEMICONDUCTOR INTEGRATED CIRCUIT AND INSPECTION AND ANALYZING METHOD

(75) Inventor: Masaaki Sugimoto, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/219,349

(22) Filed: Dec. 23, 1998

(30) Foreign Application Priority Data

Dec. 25, 1997 (JP) .............................................. 9-355926

(51) Int. Cl.$^7$ ........................... G06F 7/60; G06F 17/10; G06F 17/50

(52) U.S. Cl. ................................ 703/2; 703/13; 716/4; 716/19

(58) Field of Search ....................... 716/19; 702/83–84; 382/145, 149; 703/2, 13

(56) References Cited

U.S. PATENT DOCUMENTS

| | | | | |
|---|---|---|---|---|
| 5,240,866 A | * | 8/1993 | Friedman et al. | 702/35 |
| 5,598,341 A | * | 1/1997 | Ling et al. | 700/110 |
| 5,761,064 A | * | 6/1998 | La et al. | 700/110 |
| 5,838,951 A | * | 11/1998 | Song | 716/19 |
| 5,913,105 A | * | 6/1999 | McIntyre et al. | 438/16 |
| 5,923,430 A | * | 7/1999 | Worster et al. | 356/394 |
| 5,933,522 A | * | 8/1999 | Sugimoto | 382/149 |
| 5,946,214 A | * | 8/1999 | Heavlin et al. | 700/121 |
| 5,982,920 A | * | 11/1999 | Tobin et al. | 382/145 |
| 5,991,699 A | * | 11/1999 | Kulkarni et al. | 702/83 |
| 6,002,989 A | * | 12/1999 | Shiba et al. | 702/84 |
| 6,028,664 A | * | 2/2000 | Cheng et al. | 356/237.4 |
| 6,091,846 A | * | 7/2000 | Lin et al. | 382/145 |
| 6,185,324 B1 | * | 2/2001 | Ishihara et al. | 382/149 |
| 6,185,707 B1 | * | 2/2001 | Smith et al. | 714/724 |

FOREIGN PATENT DOCUMENTS

| | | |
|---|---|---|
| JP | 61-23327 | 1/1986 |
| JP | 4-278556 | 10/1992 |
| JP | 7-221156 | 8/1995 |
| JP | 8-124977 | 5/1996 |

OTHER PUBLICATIONS

Sugimoto et al.; "Yield enhancement using a memory expert system linked to the wafer inspection tool", IEEE/SEMI, pp. 282–288; Nov. 1995.*

McIntyre et al.; "Applying yield impact models as a first pass in upgrade decisions", IEEE/SEMI; pp. 147–149; Nov. 1994.*

Sakata et al.; "Quality control and diagnostic system for LSI fabrication"; ISSM '94; pp. 187–191; Jun. 1994.*

Pukite et al.; "Defect cluster analysis for wafer–scale integration", IEEE Trans. Semicond. Manuf.; pp. 128–135; Aug. 1990.*

Nurani et al.; "Development of an optimal sampling strategy for wafer inspection", ISSM '94; pp. 143–146; Jun. 1994.*

(List continued on next page.)

Primary Examiner—Kevin J. Teska
Assistant Examiner—Hugh Jones
(74) Attorney, Agent, or Firm—Young & Thompson

(57) ABSTRACT

An apparatus and a method for inspecting and analyzing a semiconductor integrated circuit can qualitatively and quantitatively distinguish defects caused by design and other defects by analyzing the kind and frequency of divisors between intervals of respective faulty elements. An interval $|\Delta x|$ in an X-direction, an interval $|\Delta y|$ in a Y-direction and an interval $|\Delta xy|$ derived by mulitplying the X-coordinate and the Y-direction between faulty elements with each other in an XY orthogonal coordinate system are calculated. Divisors for respective values of the intervals $|\Delta x|$, $|\Delta y|$ and $|\Delta xy|$ and number $\Sigma m$ of each divisor, are calculated. A relationship between a distribution of the faulty elements and a design standard for the kind and number $\Sigma m$ of the divisors for circuit being tested is evaluated.

16 Claims, 12 Drawing Sheets

OTHER PUBLICATIONS

McCormack; "Automated correlation of electrical failures to in–line inspections in a submicron semiconductor wafer fab"; IEE Coll. Semicond. Process.—Quality through Measurement; pp. 6/1–6/5; 1994.*

Durham et al.; "A statistical method for correlating in–line defectivity to probe yield", IEEE/SEMI; pp. 76–77; Sep. 1997.*

Harris et al.; "Estimates of integrated circuit yield components from in–line inspection data and post–process sort data"; IEEE/SEMI; pp. 150–155; Sep. 1997.*

Shindo et al.; "Excursion detection and source isolation in defect inspection and classification", 2nd Int. Wksp. Statistical Metrology; pp. 90–93; Jun. 1997.*

Perera et al.; "Micromasking of plasma etching due to bacteria: a yield detractor for ULSI"; IEEE Trans. Semicond. Manuf.; pp. 577–580; Nov. 1996.*

Nurani et al; "In–line defect sampling methodology in yield management an integrated framework"; IEEE Trans. Semicond. Manuf.; pp. 506–517; Nov. 1996.*

Stamenkovic et al.; "Modeling of integrated circuit yield loss mechanisms"; IEEE Trans. Semicond. Manuf.; pp. 270–272; May 1996.*

Tomlinson et al.; "In–line inspection to wafer test correlation"; IEEE/SEMI; pp. 100–102; Nov. 1996*

Okabe et al.; "Final visual inspection system for LSI packages"; Proc IECON '93; pp. 1877–1881; Nov. 1993.*

Cunningham; "The use and evaluation of yield models in integrated circuit manufacturing"; IEEE Trans. Semicond. Manuf; pp. 60–71; May 1990.*

Castrucci et al.; "Ultilizing an integrated yield management system to improve the return on investment in IC manufacturing"; IEEE/SEMI Int. '91; pp. 25–29; May 1991.*

Khera et al.; "Knowledge extraction techniques for expert system assited wafer screening"; IEEE/SEMI '90; pp. 44–49; May 1990.*

Hamada et al.; "Automated pattern inspection system for PCB photmaks using design pattern comparison method"; IECON '90; pp. 780–785; Nov. 1990.*

Serizawa et al.; "A false alarm reduction method for PWB pattern inspection system"; Proc. Electronic Manuf. Tech. Symp; pp. 346–349; Apr. 1989.*

Tochtrop; "Integrated measurement and analysis concept at SMST, a defect management system"; IEEE/SEMI '96; pp. 86–91; Nov. 1996.*

Radigan et al.; "Using full wafer defect maps as process signatures to monitor and control yield"; IEEE/SEMI '91; pp. 129–135; May 1991.*

Pierzynska et al.; "Built–in self–test for large embedded PLAs"; VLSI Test Symp.; pp. 73–78; Apr. 1992.*

Collica et al.; "SRAM bitmap shape recognition and sorting using neural networks"; IEEE Trans. Semicond. Manuf.; pp. 326–332; Aug. 1995.*

Tsujide et al.; "Automatic memory failure analysis using an expert system in conjuction with a memory tester/analyzer"; Reliability Physics Symp.; pp. 184–189, Mar. 1993.*

* cited by examiner

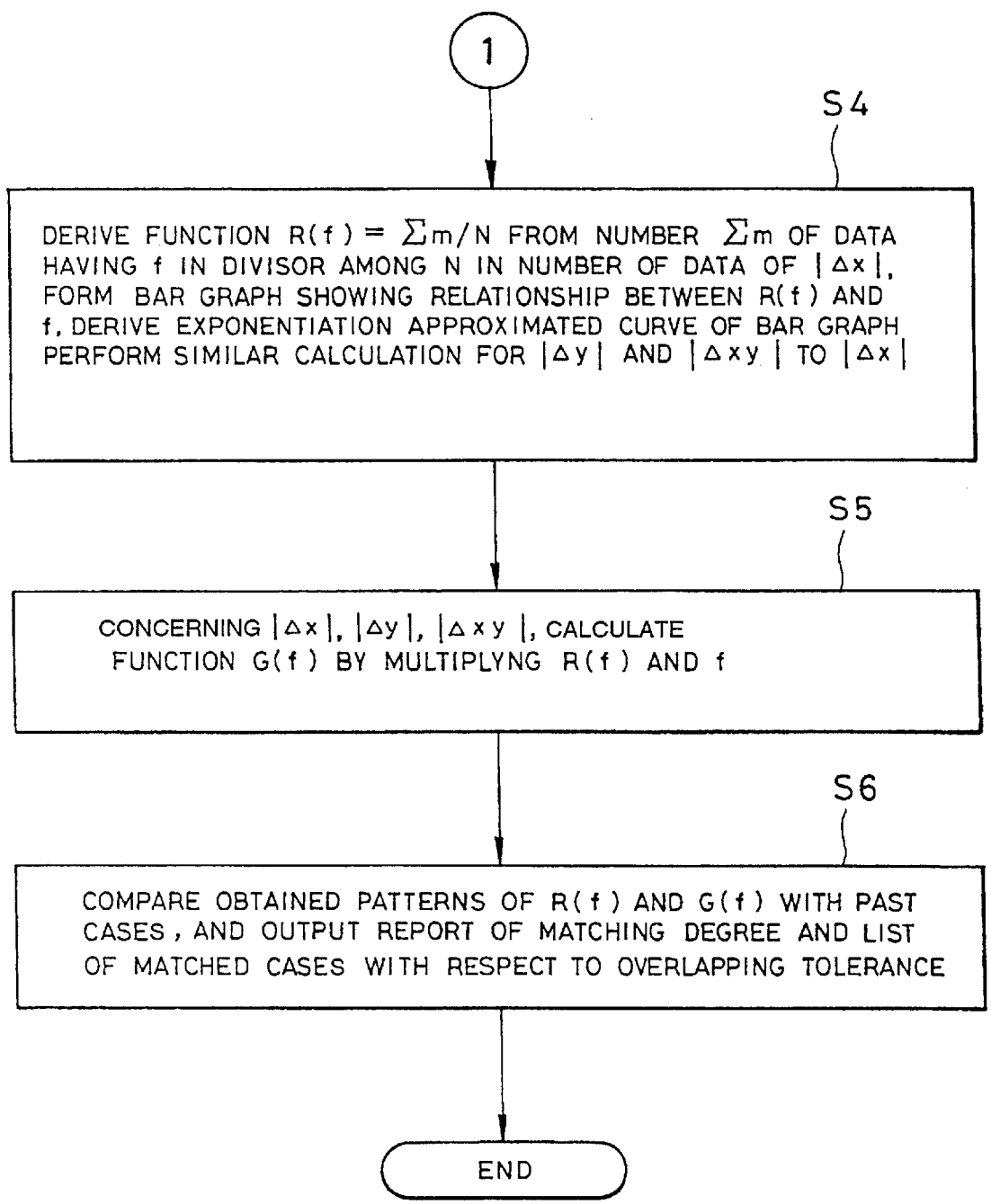

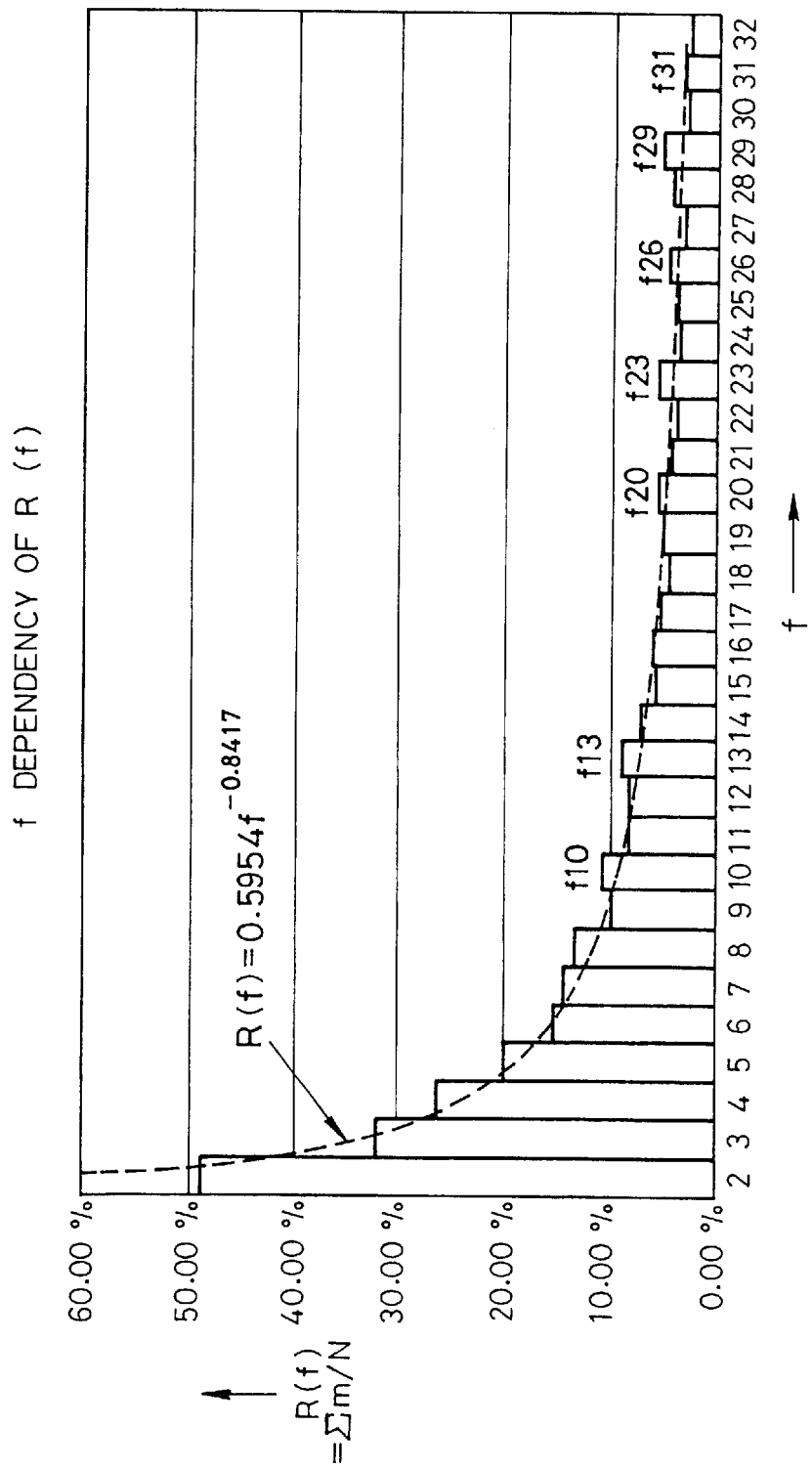

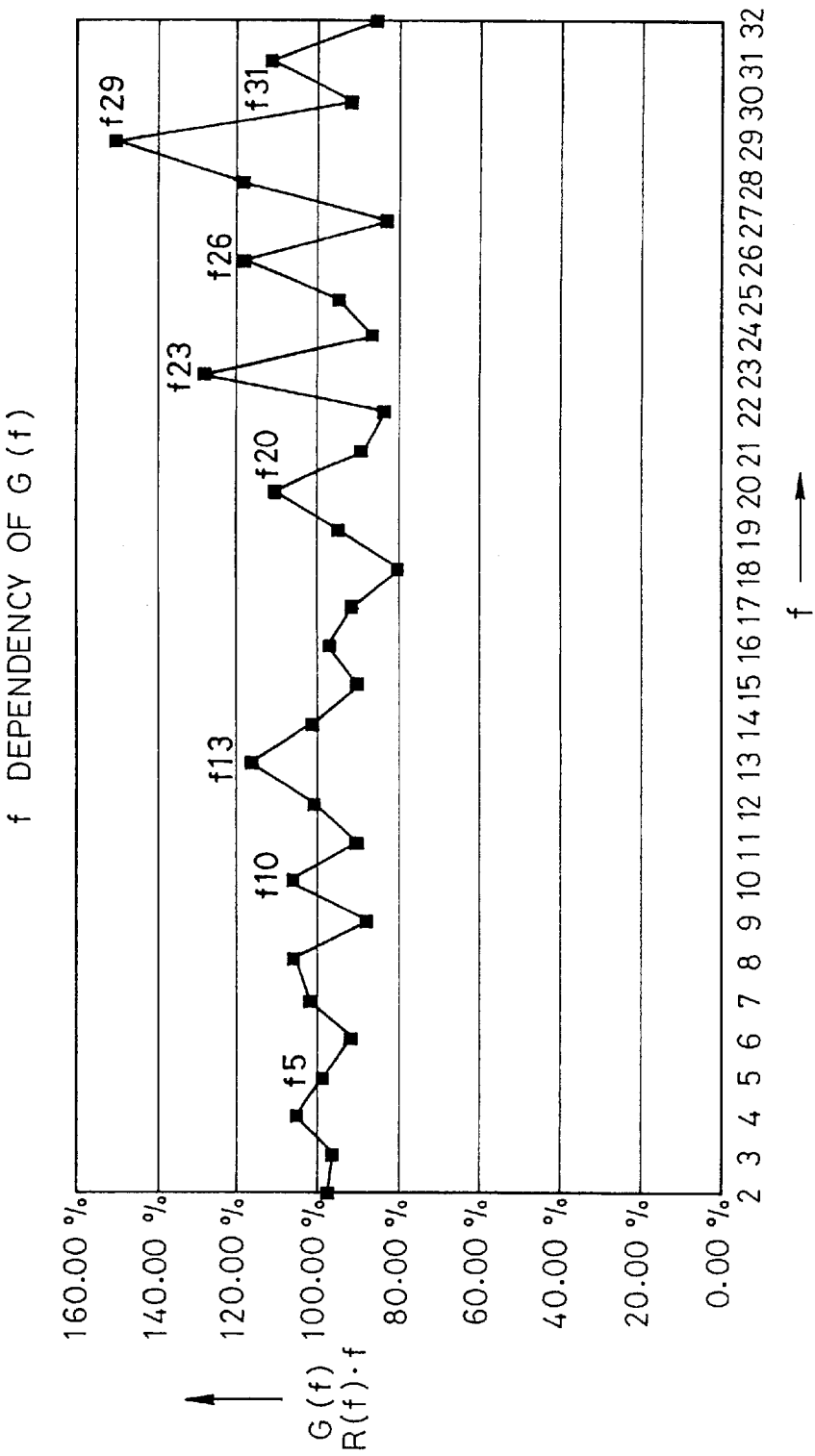

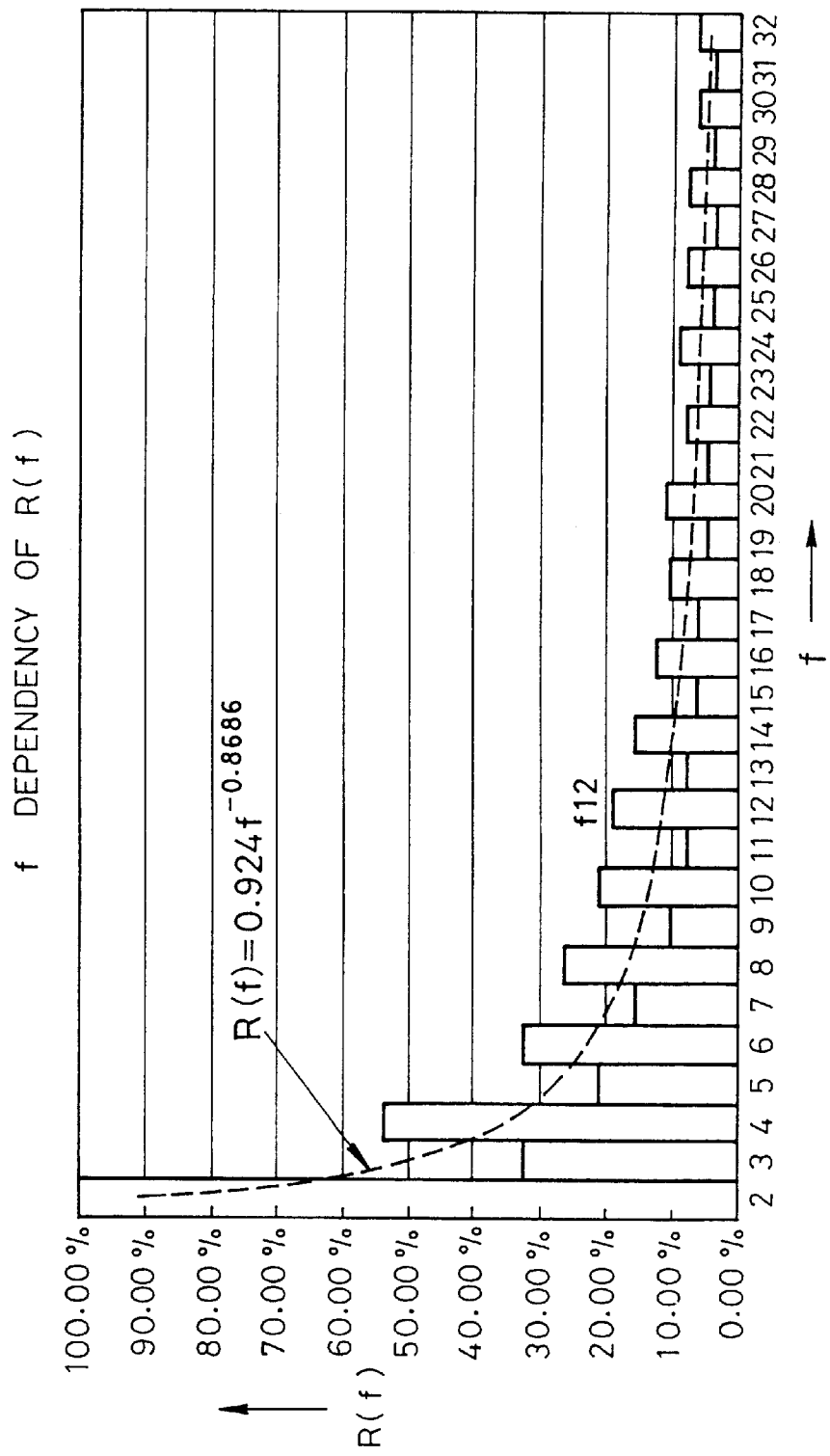

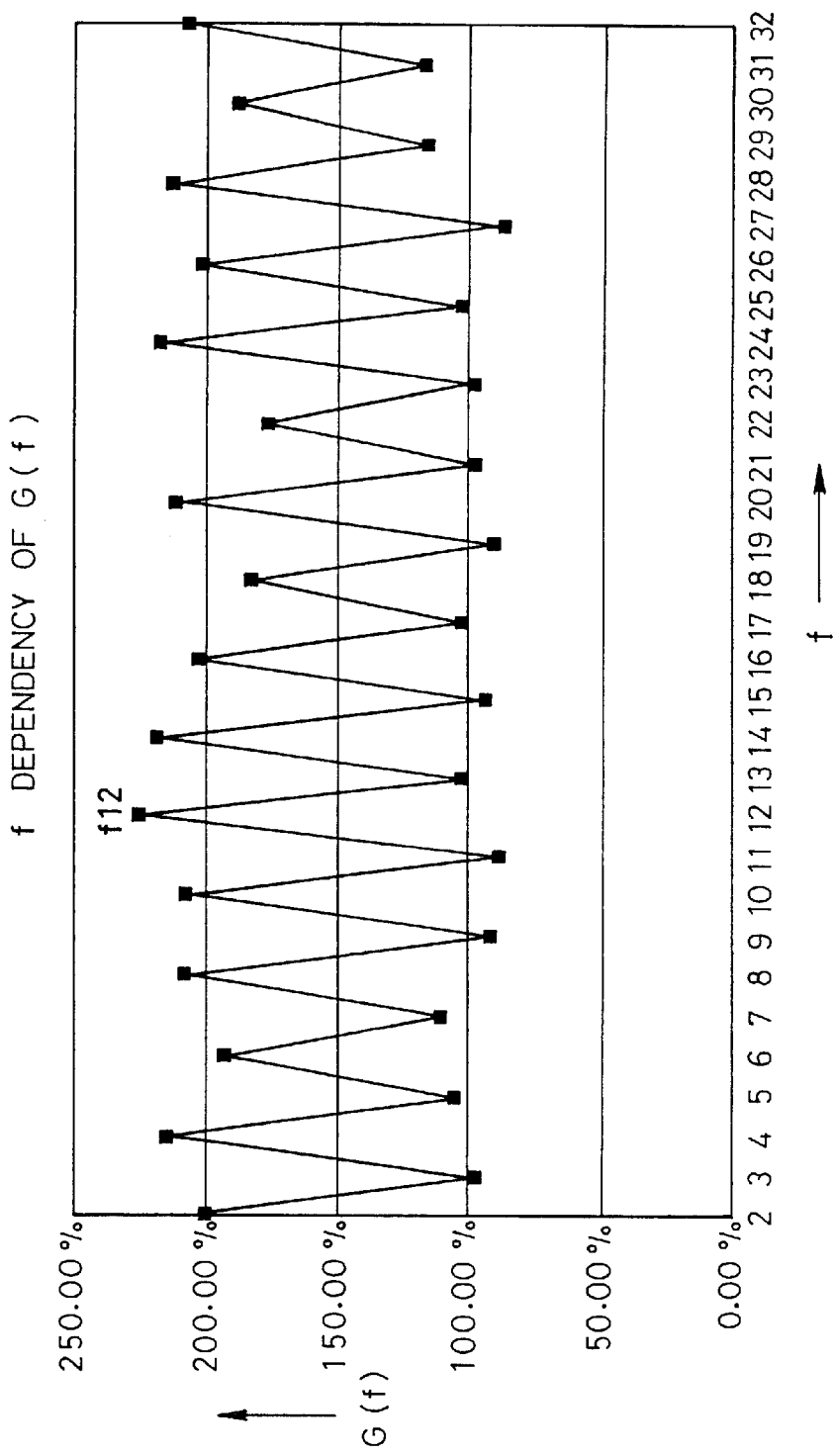

BIT MAP ILLUSTRATING
AN EXAMPLE OF
FAULTY ELEMENT
DISTRIBUTION

INSPECTION AND ANALYZING APPARATUS FOR SEMICONDUCTOR INTEGRATED CIRCUIT AND INSPECTION AND ANALYZING METHOD

BACKGROUND OF THE INVENTION

1. Field of the Invention

The present invention relates generally to an inspection and analyzing apparatus for a semiconductor integrated circuit, and a method therefor. More particularly, the invention relates to an inspection and analyzing system for a semiconductor integrated circuit that includes circuit elements arranged on a semiconductor.

2. Description of the Related Art

In inspection and analysis of an integrated circuit that has been constructed by arranging circuit elements on a semiconductor, a distribution of faulty circuit elements can be visually perceived by plotting the positions of faulty circuit circuit elements.

For example, a circuit for driving the circuit element group is divided into blocks. If all circuit elements involved in each block fail, there has been a block failure. On the other hand, if all of the faulty circuit elements having a common wiring, there has been a wiring failure. Furthermore, when a failure occurs in a single circuit element, a one bit failure has occured. On the other hand, when adjacent circuit elements fail in a group, there has been a group failure.

Such an inspection analysis and analyzing method is know as bit map analyzing and is effetive for failure analysis of semiconductor integrated circuit device, such as LSI memories and the like. However, when the number of the circuit elements exceeds about a million manual analysis of all of the causes of faulty circuit elements is difficult.

On the other hand, Japanese Unexamined Patent Publication No. Showa 61-23327 discloses a technology in which a portion where a failure has occurred is detected to find an error in a fabrication process on the basis of a distribution of kind of the failure. Namely, instead of testing a fabrication line, a faulty device is inspected to detect where the failures occurred.

For example, in a storage device, when adjacent two capacitors have a short portion through a substrate due to absence of a necessary field oxide, failure is indicated for two bits, i.e. each bit of a corresponding column and row of a memory array. Then, on the basis of a failure pattern of an address selection (ADSEL) algorithm, the faulty portion can be located.

Then, a distribution of kinds of defect in the array of of the storage device and the distribution of particular date are compared data in the past to evaluate whether time, temperature and material has not be provided according to a specification in a particular process of the fabricating operation. Then, the particular faulty mechanism is replaced.

In the technology disclosed in Japanese Unexamined Patent Publication No. Showa 61-23327, it has not been possible to distinguish between a defect caused by a design and detect caused by a fabrication process. Therefore, in the semiconductor integrated circuit, in case of distribution of the faulty elements which is visually perceived to be irregular, prediction of a cause of failure based on the shape of the distribution becomes difficult.

SUMMARY OF THE INVENTION

The present invention has been worked out in order to solve the problem in the prior art. Therefore, it is an object of the present invention to provide and inspection and analyzing apparatus of a semiconductor integrated circuit, and a method therefor, which can qualitatively and quantitatively distinguish a cause of a failure between a defect due to design and a defect due to other causes by analyzing the kind and frequency of a divisor of an interval between respective faulty elements.

According to one aspect of the present invention, an inspection and analyzing apparatus of a semiconductor integrated circuit comprises:

interval calculating means for calculating an interval $|\Delta x|$ in an X-direction, an interval $|\Delta y|$ in a Y-direction and an interval $|\Delta xy|$ derived by multiplying the X-coordinate and the Y-direction between faulty elements with each other in an XY orthogonal coordinate system representative of a positional relationship of circuit element groups arranged on a semiconductor element;

divisor calculating means for calculating divisors for respective values of the intervals $|\Delta x|$, $|\Delta y|$ and $|\Delta xy|$ and further calculating a number $\Sigma m$ of each divisor; and judgment means for evaluating a relationship between a distribution of the faulty elements and a design standard for the kind and number $\Sigma m$ of the divisors for the circuit being tested. Then, the judgment means may derive respective functions of $R(x, f) = \Sigma m/Nx$, $R(y, f) = \Sigma m/Ny$, $R(xy, f) = \Sigma m/Nxy$ when total numbers of respective values of the intervals $|\Delta x|$, $|\Delta y|$ and $|\Delta xy|$ are Nx, Ny and Nxy, respectively, and evaluate a relationship between a distribution of the faulty element and a design standard for a distribution condition of the values of the divisor f.

Also, the judgment means may further derive functions $R(x, f)*f$, $R(y, f)*f$ and $R(xy, f)*f$ by multiplying respective ones of the functions by f, and evaluating of a relationship between a distribution of the faulty element and a design standard for a distribution condition of the values of the divisor f.

The judgment means may indicate that the faulty elements are in irregular positional relationship when the individual values of each of the functions corresponding to a prime number in the divisor f is greater than that of other values of the divisor. When irregular positional relationship are found, a fabrication is probably at fault.

The judgment means may indicate that the faulty element has a relationship with the design standard when respective individual values of respective functions corresponding to an even number among the the divisors f is majority in comparison with those of other divisors.

According to another aspect of the present invention, an inspection and analyzing method of a semiconductor integrated circuit comprises:

a step of exhaustively calculating an interval $|\Delta x|$ in an X-direction, an interval $|\Delta y|$ in a Y-direction and an interval $|\Delta xy|$ derived by multiplying the X-coordinate and the Y-direction between faulty elements with each other in an XY orthogonal coordinate system representative of positional relationship of circuit element groups arranged on a semiconductor;

a step of calculating divisors for respective values of the intervals $|\Delta x|$, $|\Delta y|$ and $|\Delta xy|$ and further calculating number $\Sigma m$ of each divisor; and a judgment step of evaluating a of relationship between a distribution of the faulty element and a design standard depending upon the kind and number $\Sigma m$ of the divisors.

Then, the judgment step includes a step of deriving respective functions of $R(x, f)=\Sigma m/Nx$, $R(y, f) \Sigma m/Ny$, $R(xy, f)=\Sigma m/Nxy$ when total numbers of respective values of the intervals $|\Delta x|$, $|\Delta y|$ and $|\Delta xy|$ are Nx, Ny and Nxy, respectively, and a step of indicating a relationship between a distribution of the faulty element and a design standard depending upon a distribution condition of respective values in relation to the divisor f, with reference to the values relative of each individual f of each of the functions.

Also, the judgment step may further comprise a step of deriving functions $R(x, f)*f$, $R(y, f)*f$ and $R(xy, f) *f$ by multiplying respective of the functions by f, and a step of evaluating a relationship between a distribution of the faulty elements and a design standard depending upon a distribution condition of respective values of the divisor f.

In the operation of the present invention, the inspection and analyzing apparatus and method of a semiconductor integrated circuit exhaustively calculates an interval $|\Delta x|$ in an X-direction, an interval $|\Delta y|$ in a Y-direction and an interval $|\Delta xy|$ derived by multiplying the X-coordinate and the Y-coordinate between faulty elements with each other in an XY orthogonal coordinate system representative of positional relationship of circuit element groups arranged on a semiconductor, calculates divisors for respective values of the intervals $|\Delta x|$, $|\Delta y|$ and $|\Delta xy|$ and further calculates a number $\Sigma m$ of each divisor, and evalutes a relationship between a distribution of the faulty elements and a design standard depending upon kind and number $\Sigma m$ of the divisors.

Most LSI memories are designed to have a circuit design and layout according to a rule of exponentiation of 2 for making one electrode in common with two memory elements, for driving wiring per a unit of two wires or four wires, for arranging circuit driving four wires symmetrically (per 8 wires), and for driving sixteen wires by one driving circuit. Namely, since the design rule of the memory does not include prime numbers of 3, 5, 7, 9, 11, 13, 17, 19 . . . , the distribution of the faulty elements includes prime numbers other than two in the divisors of the interval of the faulty elements, it can be predicted that failure is caused by something other than circuit design or layout design.

Accordingly, by the present invention, when the distribution of the divisors of the intervals between the faulty elements includes the prime number having no relation with a design rule for the circuit and a relationship with with the yield of the fabrication process for the semiconductor integrated circuit is checked, effective means for detecting and analyzing the cause of the failures can be provided.

BRIEF DESCRIPTION OF THE DRAWINGS

The present invention will be understood more fully from the detailed description given herebelow and from the accompanying drawings of the preferred embodiment of the present invention, which, however, should not be taken to be limitative to the invention, but are for explanation and understanding only.

In the drawings:

FIGS. 3A and 3B are flowcharts showing process operation steps of an embodiment of the present invention;

FIG. 5 shows an example of a relationship between a function R(f) and a divisor f, in the case of high irregularity of faulty element distribution;

FIG. 6 shows an example of a relationship between a function G(f) and a divisor f, in the case of high irregularity of faulty element distribution;

FIG. 7 shows an example of a relationship between a function R(f) and a divisor f, in the case of high regularity of faulty element distribution;

FIG. 8 shows an example of a relationship between a function G(f) and a divisor f, in the case of high regularity of faulty element distribution;

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessarily obscuring the present invention.

Figure 1:
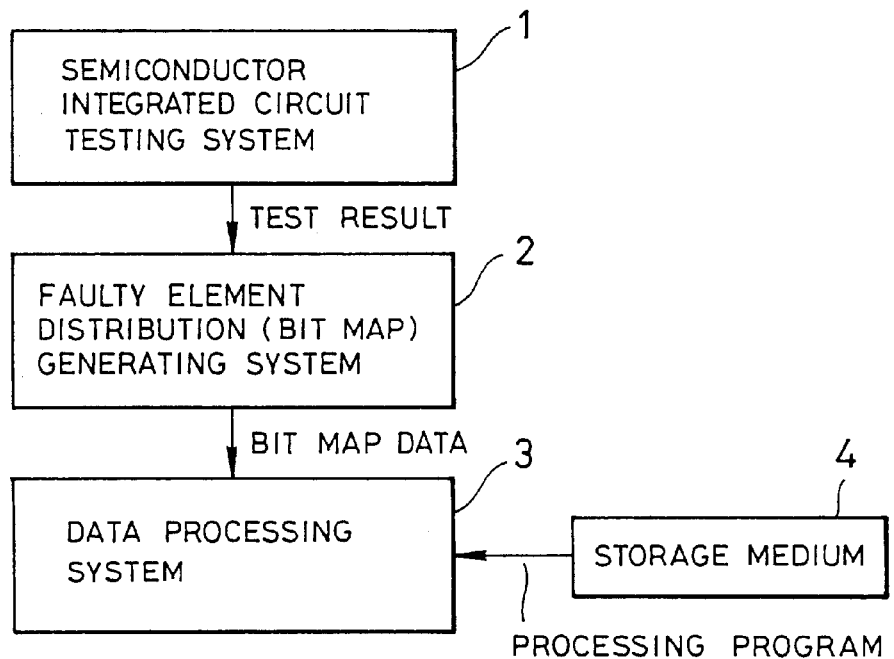
FIG. 1 is an illustration showing a general construction of an LSI inspection and analyzing system, to which the present invention is applied.

FIG. 1 is a block diagram showing a general construction of an inspection and analyzing system of a semiconductor integrated circuit, to which the present invention is applied. In FIG. 1, the semiconductor integrated circuit testing system 1 executes a process for an LSI to be tested in accordance with a predetermined test program and to generate a test result of the LSI tested.

A faulty element distribution (bit map) generating system 2 outputs a result of re-arrangement of electrical address coordinates of the faulty elements included in the test result adapting to a layout on the semiconductor circuit, in a form of a faulty element distribution, namely a bit map.

Figure 10:
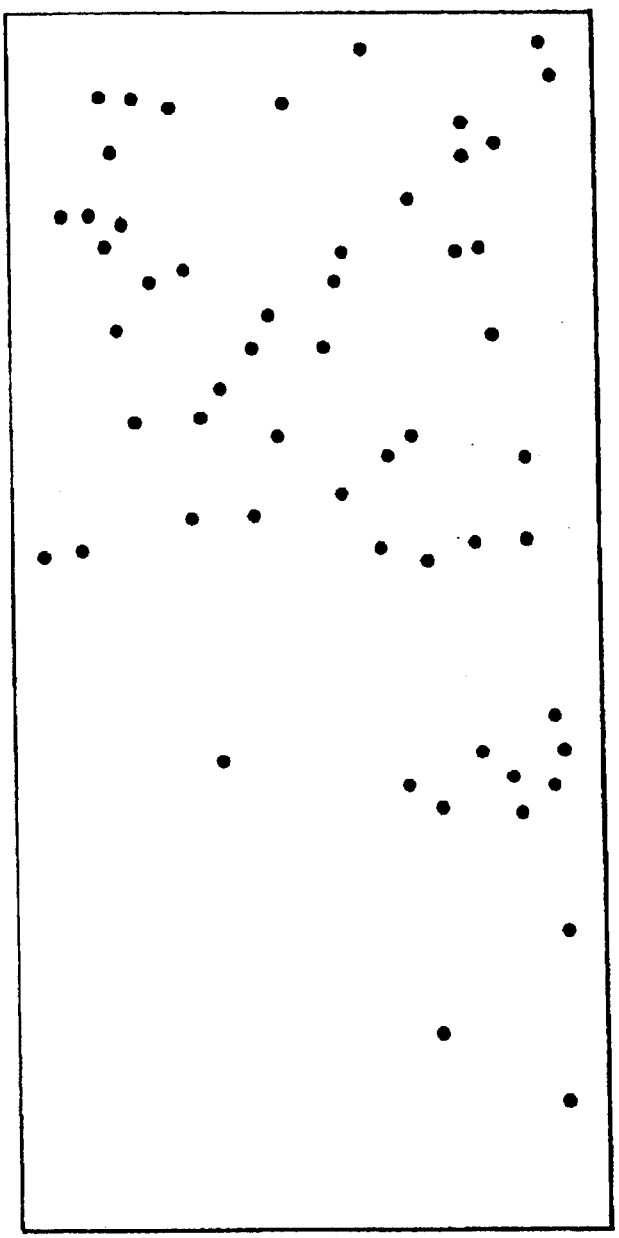
FIG. 10 is an illustration shown an example of bit map as distribution of faulty element distribution.

A data processing system 3 inspects and analyzes the bit map according to the present taking bit map data (shown in FIG. 10) as an input. A program for the inspection and analyzing process is stored in a storage medium 4 such as ROM (Read Only Memory) HDD(Hard Disk Drive) device and so on.

Figure 2:
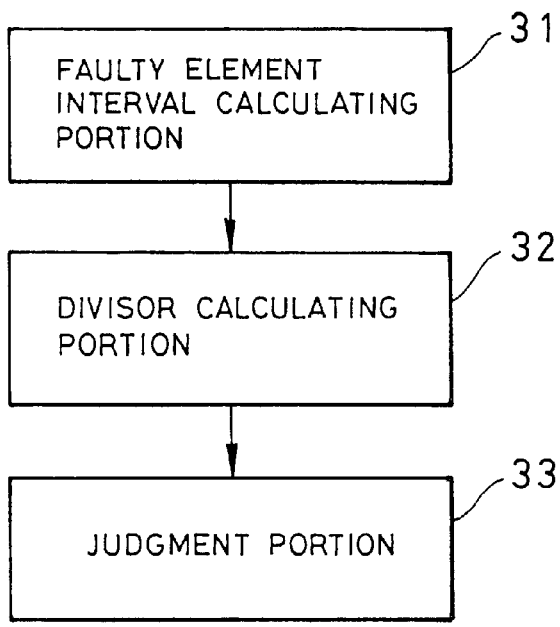
FIG. 2 is a block diagram showing a general function of a data processing unit 3 in FIG. 1.

As shown in FIG. 2, the data processing system 3 includes a faulty element interval calculating portion 31 for calculating an interval between the faulty elements, a divisor calculating portion 32 for calculating kind and number of divisors f included in the interval between the faulty elements, and a judgment portion 33 for evaluating a relationship between a distribution of the faulty elements and a design standard for the circuit being tested depending upon kind and number of those divisors.

Figure 3A:
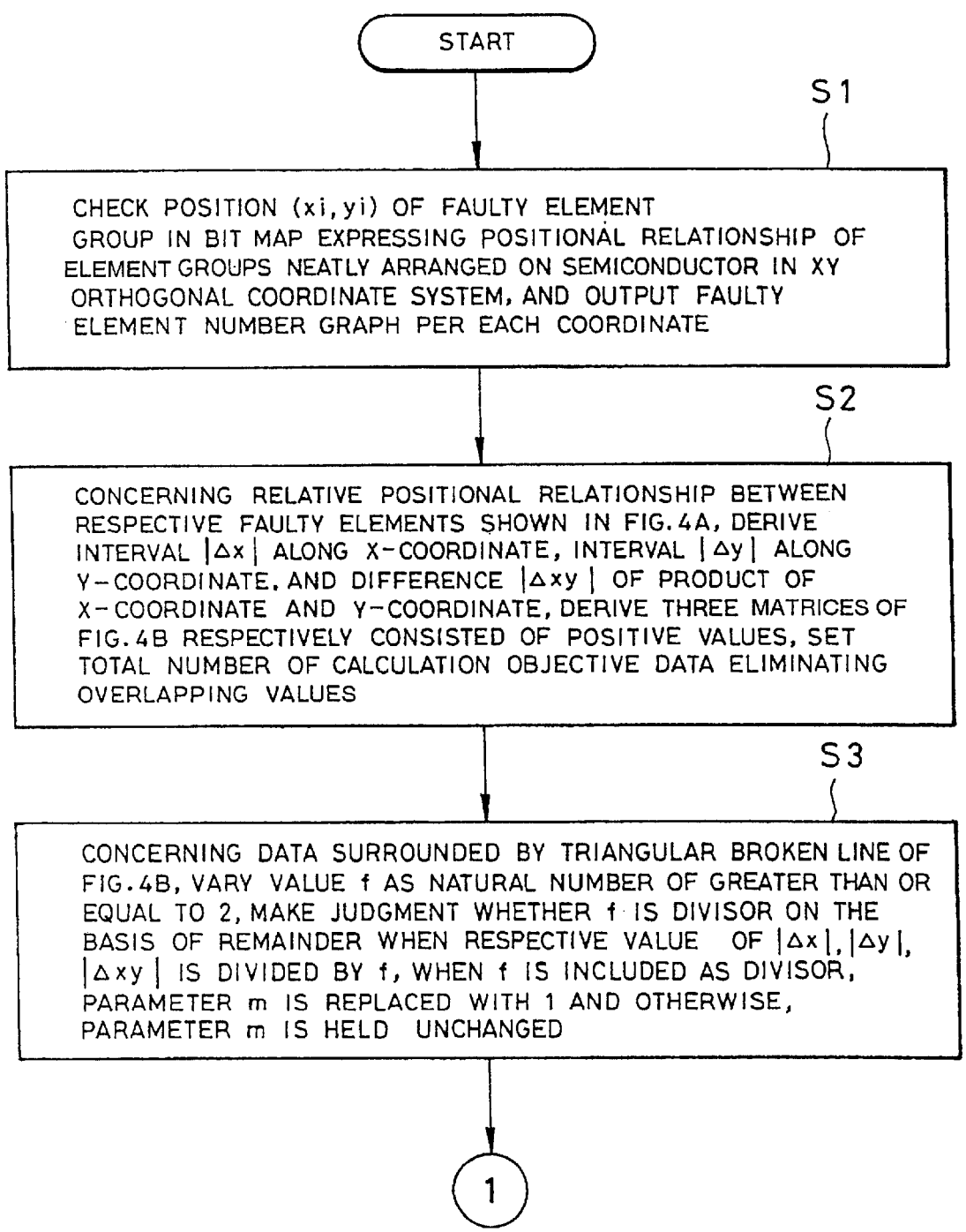

FIGS. 3A and 3B are flowcharts showing a flow of a process of the data processing system 3 shown in FIG. 1 and also a flowchart showing a process procedure of respective portions 31 to 33 of FIG. 2. Operation of the shown embodiment of the present invention will be discussed with reference to FIG. 3.

Figures 4A, 4B:
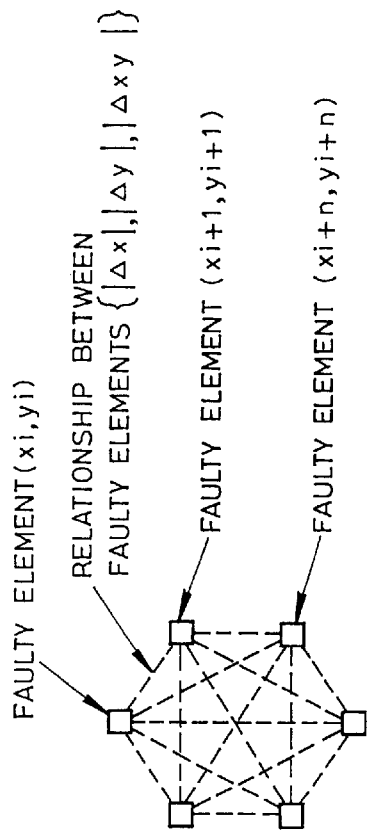
FIG. 4A is an illustration showing an example of an arrangement of faulty elements on a bit map.
FIG. 4B is an illustration showing each data array of interval of faulty elements.

In a bit map expressing a positional relationship of circuit element groups neatly arranged on the memory LSI as an object for inspection, in an XY orthogonal coordinate system, positions of all of the faulty element groups (xi, yi) represented by square in FIG. 4A are checked exhaustively to check X-coordinates and Y-coordinates of the faulty element numbers and XY coordinate dependency. Namely, a graph expressing a number of faulty elements per each coordinate position is output (step S1).

Next, concerning relative positional relationships between respective faulty elements shown by broken lines of FIG. 4A, an absolute value of an interval $|\Delta x|$ along the X-coordinates, an absolute value of an interval $|\Delta y|$ along the Y-coordinates, and an absolute value of a difference $|\Delta xy|$ of products of X-coordinates and Y-coordinates of respective faulty elements are calculated. A reason why $|\Delta xy|$ is calculated is for performing detection and analysis of cause of failure depending upon combinations of the X-coordinates and the Y-coordinates.

On the basis of the foregoing calculation, three kinds of matrixes shown in FIG. 4B are generated. Namely, the three kinds of matrixes are a matrix of the interval $|\Delta X|$ along the X-coordinates, and a matrix of the interval $|\Delta y|$ along the Y-coordinates between respective faulty elements, and a matrix of the difference $|\Delta xy|$ of the products of the X-coordinates and Y-coordinates.

Since overlapping data are included in these matrixes, data to be actually calculated are only data group (N in total number) surrounded by triangular broken line in FIG. 4B. Then, total number of data to be object for arithmetic operation is set as N (step S2).

Next, concerning data surrounded by the triangular broken line of FIG. 4B, respective values of $|\Delta x|$, $|\Delta y|$, $|\Delta xy|$ are checked whether these values are divisible by f (f is a natural number greater than or equal to 2, and the maximum value v does not exceed ½ of X, Y and XY). Namely, check is performed where the data group surrounded by the triangular broken line shown in FIG. 4B have respective f as divisor. When the values are divisible, a value of a parameter m is set to one (1), and, if the value is not divisible, the value of the parameter m is held unchanged (step S3).

Next, among N data within a region surrounded by the triangular broken lines in the matrix of $|\Delta x|$, a function $R(f)=\Sigma m/N$ is derived on the basis of number $\Sigma m$ of data having f as divisor. Then, from a graph showing a relationship between the function $R(f)=\Sigma m/N$ and f shown in FIG. 5, a kind and a content rate of an arbitrary divisor f included in an interval between respective faulty elements in the X-axis direction can be known.

The bar graph shown in FIG. 5 represents actually measured values of R(f) and a broken line graph is an exponentiation approximated curve $R(f)=0.5954*f^{-0.8417}$ (step S4).

At this time, when the relationship between the faulty element distribution and f is difficult to read from a relationship between R(f) and f, a graph shown in FIG. 6 is established to show a relationship between a function G(f), derived by multiplying f times R(f) and f, decoding becomes easier (step S5).

In this case, it has been shown clearly that there are faulty elements distributed in element intervals including prime numbers 5, 13, 23, 29 and 31 as divisors in large proportion, among divisors f. The fact that the prime numbers appear as the divisor in large proportion means that the failure is not caused due to design but is caused due to a fabrication process (lowering of yield). Thus, a feedback to a designer is unnecessary, and rather, a feedback to other than designer becomes necessary.

Concerning $|\Delta y|$ and $|\Delta xy|$, similar processes to that for $|\Delta x|$ is performed.

Then, finally, by comparing patterns of the obtained R(f) and G(f) of past case respectively, a matching degree and a matching case list with respect to an overlapping tolerance (for example, an offset of values of R(f) and G(f) relative to respective f value is less than 10% of a reliable level, and so on) is output as a report (step S6).

When the element to be inspected is DRAM element, for example, in a circuit design, at first, a four bit basic mask consisted of row 1 bit×column 1 bit, is designed. By aligning two basic masks in row direction, one set of row 2 bits× column 4 bits is established. By arraying 512 sets, a mask of row 1024 bits×column 4 bits is formed.

By sequentially arranging the masks, a design of 16 Mbits DRAM of row 2048 bits×column 4096 bits+peripheral circuit+common wiring+peripheral circuit+row 2048 bits×column 4096 bits, can be completed.

At this time, circuits driving each row and each column are hierarchical circuits, which are arranged in an exponentiation of 2, an exponentiation of 4 or an exponentiation of 8 or a combination of the exponentiation of 2 and the exponentiation of 4 or the exponentiation of 8. For example, when a parent circuit drives two, four or eight child circuits, the child circuit also drives two, four or eight grand child circuit, to establish a hierarchical structure.

In the foregoing designing process, numbers used are all 2 powered by n. Namely, in failure of DRAM caused by design, the failure is caused in the interval all having a divisor of 2 powered by n. For example, when a failure is caused in design of the driving circuit of wiring of 1024 (th) in a column direction (since address is started from 0, column address is 1023), an address of column commonly driven by the driving circuit may also be frequently influenced. Therefore, it is quite likely that the failure is not caused in the 1024 (th) column alone, but can be caused in a plurality of columns.

In this case, in addition to the faulty address 1023 and adjacent addresses 1022 and 1024, failure can be distributed to 2n of 1021, 1025 and so forth, 4n of 1019, 1027 and so forth, 8n, 16n or further possibly to be distributed to 2 powered by 10, such as 2047, 3071, 4095 and so forth.

Accordingly, the failure at the interval other than 2 powered by n, it can be predicted that there is high likelihood that the failure is caused by irregular cause other than cause of design, such as cause in the fabrication process, such as deposition of dust, dirt or so forth.

FIGS. 5 and 6 show examples of the case where irregularity of faulty element distribution is high. On the other hand, FIGS. 7 and 8 show examples of the case where regularity of faulty element distribution is high.

FIG. 7 shows a relationship between R(f) and f, and FIG. 8 shows a relationship between G(f) and f.

In FIGS. 7 and 8, in comparison with the case of FIGS. 5 and 6, since the values of R(f) and G(f) when f is an even number (including 2 powered by n) is significantly high, it can be predicted that failure is caused by design taking two faulty elements or two wiring as one set.

Furthermore, by storing relationships between f, R(f) and G(f) as examples of lowering of yield in past fabrication of the semiconductor integrated circuit, in a database, cause of failure having similar patterns can be detected in a short period with taking the values of R(f) or G(f) as keywords.

Figure 9A:
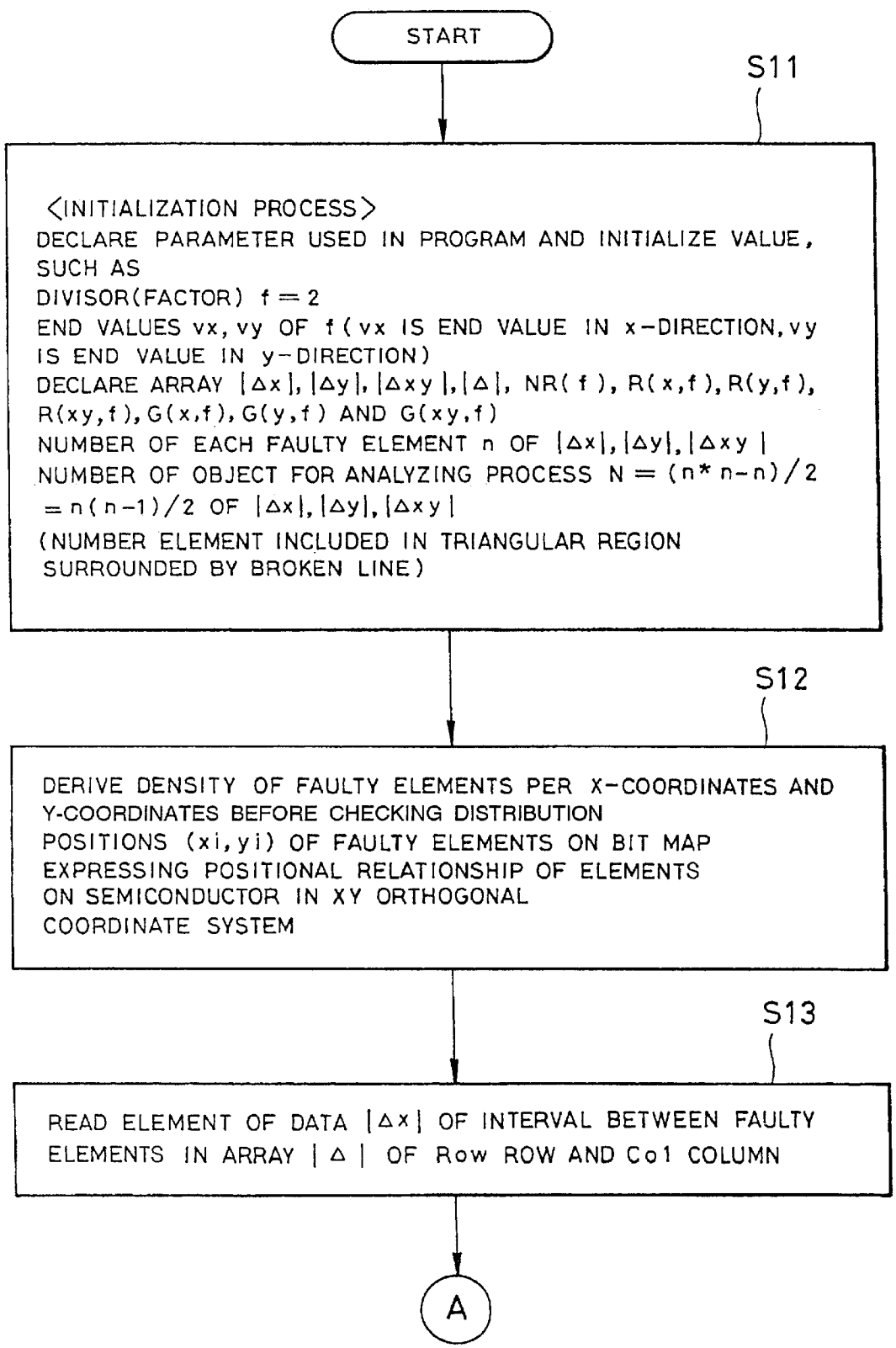
FIGS. 9A, 9B and 9C are flowcharts showing details of operation of the embodiment of the present invention.
Figure 9B:
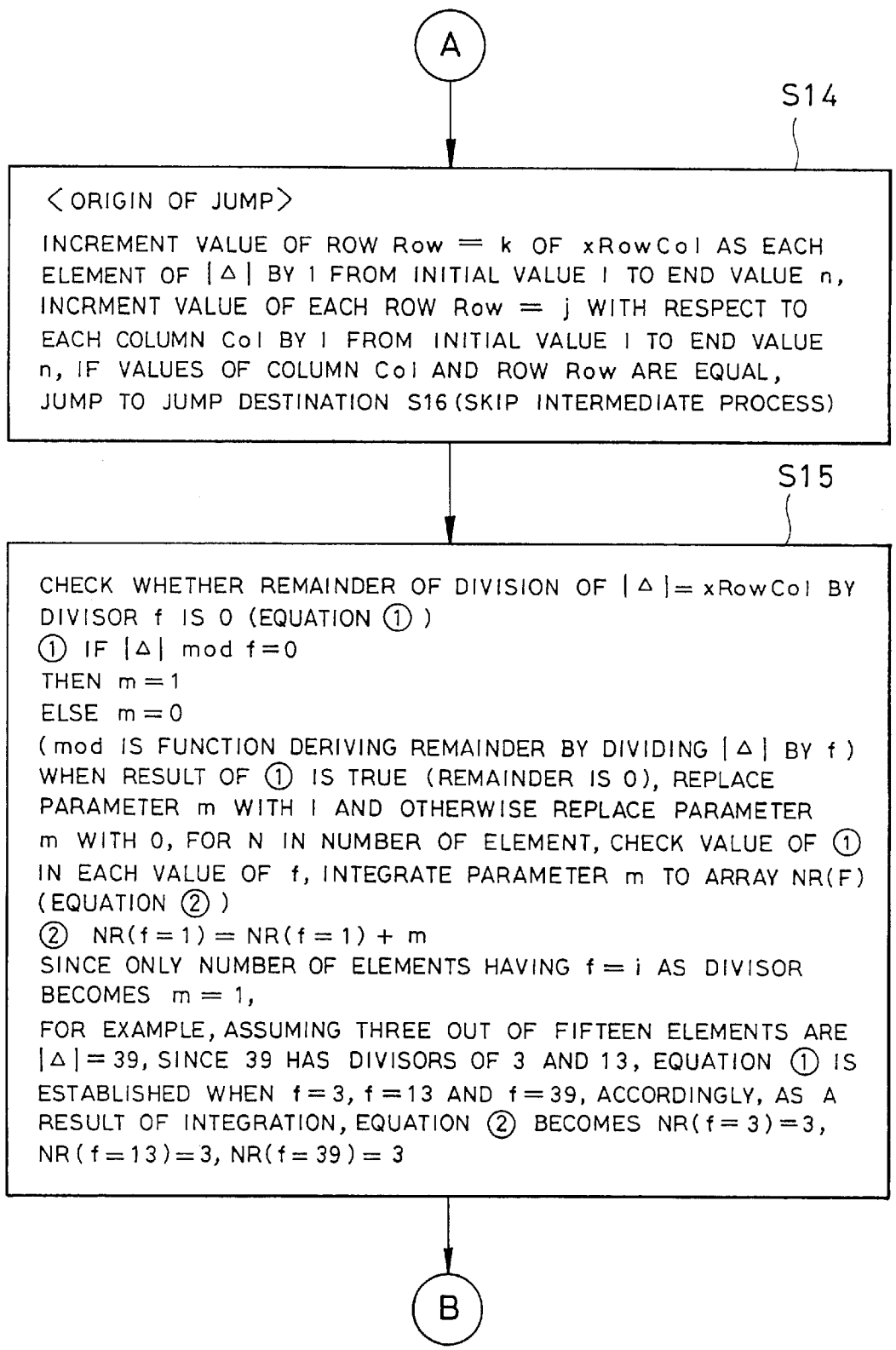
Figure 9C:
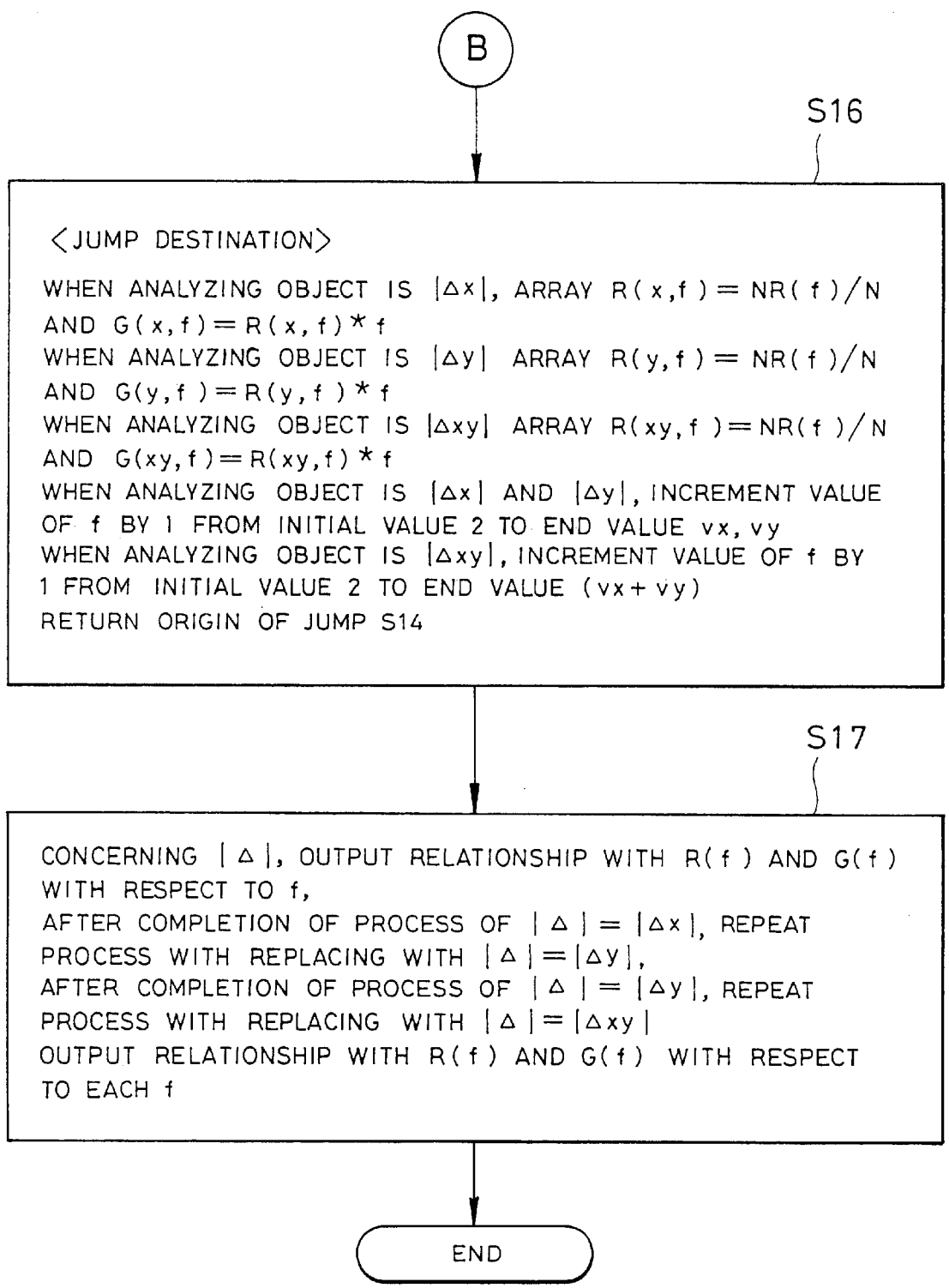

FIGS. 9A, 9B and 9C are flowcharts showing detail of steps S2 to S5 in the flowchart shown in FIG. 3. In FIG. 9A, steps S11 is a step for performing an initialization process, in which the divisor f is set at an initial value 2, and end values $v_x$ and $v_y$ (end values in x and y directions) are defined.

On the other hand, an array |Δ| is declared for reading the arrays |Δx|, |Δy|, |Δxy| shown in FIG. 4B and elements of respective data of respective arrays. Furthermore, functions R(x, f) and G(x, f) relative to |Δx|, functions R(y, f) and G(y, f) relative to |Δy| and functions R(xy, f) and G(xy, f) relative to |Δxy| and so forth are declared.

The value is initialized by declaring a parameter to be used in the program, such as each number of faulty elements n of |Δx|, |Δy|, |Δxy|, number of objects for analyzing process N=(n*n−n)/2=n(n−1)/2 and so forth.

At a next step S12, distribution positions ($x_i$, $y_i$) of the faulty elements are exhaustively checked on the bit map expressing positional relationships of the element group neatly arranged on the semiconductor, by XY orthogonal coordinate system, for deriving a faulty element density per X-coordinate and Y-coordinate.

At a next step S13, an element of data |Δx| of the interval of the faulty element is read in the array |Δ|. Then, at step S14, a value k of the row of |Δx| as respective elements of |Δ| is sequentially incremented from the initial value 1 by 1 to the end value n, and the other value j with respect to a value of each column is sequentially incremented from the initial value 1 by 1 to the end value n. At this time, when the values of the row and the column are equal to each other, a process jumps to a jump destination (S16).

At step S15, according to an equation ①, a check is made whether the interval is divisible by the divisor f or not. At this time, when a remainder is 0, a parameter m is replaced with 1 and otherwise is replaced with 0. For N in number of elements, the values of the equation ① at respective values of f are checked to integrate the parameter m to an array NR(f).

In this case, m=1 is set for number of elements having f=i as divisor. Therefore, assuming that among 15 elements, three are |Δ|=39, since 39 has 3 and 13 as divisors, the equation ① is established for three times at f=3, 13 and 39. Accordingly, as a result of integration, the equation ② is $$NR(f=3)=3$$

$$NR(f=13)=3$$

$$NR(f=39)=3$$

At step S16, the value of the divisor f is incremented by 1 and the value j of the column does not reach the end value n, the process returns to step S14 for incrementing the value j. Also, when the value k of the row does not reach the end value n, the process returns to step S14.

At step S17, a relationship of R(f) and G(f) obtained at the foregoing step relative to each f are output.

While the foregoing embodiment takes the LSI memory as the object to be inspected, the present invention is applicable for a color liquid crystal display device, a color plasma display device, a color image pick-up device, a three-color printing apparatus and so forth.

In this case, a system construction and flow of process are the same as the foregoing embodiment. However, as a divisor having close connection with a design rule, 3 is taken in addition to 2 to evaluate whether the faulty element distribution has irregular positional relationship when prime numbers other and 2 or 3 as divisor are in the majority.

Namely, a design rule multiplying 3 by exponentiation of 2 is used so that an IC handling color takes elements corresponding to three primary colors as one unit, and takes one electrode or wiring in common (2 units), and one arranging these symmetrically (4 units) are repeated.

As set forth above, according to the present invention, automatic separation of regular and irregular of faulty element distribution, is made possible. Therefore, as shown in an example of bit map in FIG. 10, even for a faulty element distribution that is visually perceived to be irregular and which was believed to be impossible to analyze visually, a cause of failure can be established.

Namely, even for discrete and low density or composite and the high density faulty element distribution, whose pattern cannot be recognized clearly by a person, by monitering R(f) and G(f), precursor phenomenon of lowering of yield due to lack of margin in design can be detected as increasing of a component of exponentiation of 2 (having a relationship with the design rule) and precursor phenomenon of failure caused by the reason other than design can be detected as increasing of component of prime number greater than or equal to 3 (no relation with design rule).

Although the present invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodied within a scope encompassed and equivalents thereof with respect to the feature set out in the appended claims.

What is claimed is:

1. An apparatus for analyzing faults in circuit elements on a semiconductor wafer, the apparatus comprising:
    interval calculating means for iteratively calculating intervals between faulty circuit elements in an X-direction |ΔX|, a Y-direction |ΔY|, and a value |ΔXY| that is a multiple of the X-coordinate times the Y-coordinate of respective faulty circuit elements;
    divisor calculating means for calculating divisors f for respective values of |ΔX|, |ΔY|, and |ΔXY| and a number Σm of each of the divisor f values; and
    judgment means for evaluating the divisor f values and Σm to determine whether a distribution of the divisors f has a binary basis.

2. The apparatus of claim 1, wherein said judgment means further evaluates whether a distribution of the divisor f values has a base-3 basis.

3. The apparatus of claim 1, wherein said judgment means derives first functions R(x,f)=Σm/Nx, R(y,f)=Σm/Ny, R(xy, f)=Σm/Nxy, where Nx, Ny, and Nxy are total numbers of the respective intervals, and evaluates distributions of the first functions versus divisor f values.

4. The apparatus of claim 3, wherein said judgment means derives second functions G(x,f)=R(x,f)*f, G(y,f) =R(y,f)*f, and G(xy,f) =R(xy,f)*f, and evaluates distributions of the second functions versus divisor f values.

5. The apparatus of claim 1, wherein said judgment means indicates that the faulty elements are in irregularly located positions when a number of the divisor f values that are prime numbers other than two is greater than a number of divisor f values that are not.

6. The apparatus of claim 1, wherein said judgment means indicates that the faulty elements are in regularly located positions when a number of the divisor f values that are binary based is greater than a number of divisor f values that are not.

7. A method for analyzing faults in circuit elements on a semiconductor wafer, the apparatus comprising the steps for:
    iteratively calculating intervals between faulty circuit elements in an X-direction |ΔX|, a Y-direction |ΔY|, and a value |ΔXY| that is a multiple of the X-coordinate times the Y-coordinate of respective faulty circuit elements;

calculating divisors f for respective values of |ΔX|, |ΔY|, and |ΔXY| and a number Σm of each of the divisor f values; and evaluating the divisor f values and Σm to determine whether a distribution of the divisor f values has a binary basis.

8. The method of claim 7, wherein the evaluating step further evaluates whether a distribution of the divisor f values has a base-3 basis.

9. The method of claim 7, wherein the evaluating step further comprises the steps for deriving first functions R(x,f)=Σm/Nx, R(y,f)=Σm/Ny, R(xy,f)=Σm/Nxy, where Nx, Ny, and Nxy are total numbers of the respective intervals, and evaluating distributions of the first functions versus divisor f values.

10. The method of claim 9, wherein the evaluating step further comprises the steps for deriving second functions G(x,f)=R(x,f)*f, G(y,f)=R(y,f)*f, and G(xy,f)=R(xy,f)*f, and evaluating distributions of the second functions versus divisor f values.

11. The method of claim 7, wherein the evaluating step further indicates that the faulty elements are in irregularly located positions when a number of the divisor f values that are prime numbers other than two is greater than a number of divisor f values that are not.

12. The method of claim 7, wherein the evaluating step further indicates that the faulty elements are in regularly located positions when a number of the divisor f values that are binary based is greater than a number of divisor f values that are not.

13. A method for separating design faults from other faults in the manufacture of a semiconductor device, the apparatus comprising the steps of:

calculating intervals between faulty circuit elements on a semiconductor device in an X-direction |ΔX|, a Y-direction |ΔY|, and a value |ΔAXY| that is a multiple of the X-coordinate times the Y-coordinate of respective faulty circuit elements;

calculating divisors f for respective values of |ΔX|, |ΔY|, and |ΔXY| and a number Σm of each of the divisor f values;

generating a distribution of the divisor f values and Σm;

indicating that the faulty circuit elements are design faults when the distribution has a binary basis; and indicating that the faulty circuit elements are not design faults when the distribution shows that a number of the divisor f values that are prime numbers other than two is greater than a number of divisor f values that are not.

14. The method of claim 13, further comprising the step of indicating whether a distribution of the divisor f values has a base-3 basis.

15. The method of claim 13, further comprising the steps of deriving first functions R(x,f)=Σm/Nx, R(y,f)=Σm/Ny, R(xy,f)=Σm/Nxy, where Nx, Ny, and Nxy are total numbers of the respective intervals, and evaluating distributions of the first functions versus divisor f values.

16. The method of claim 15, further comprising the steps for deriving second functions G(x,f)=R(x,f)*f, G(y,f)=R(y,f)*f, and G(xy,f)=R(xy,f)*f, and evaluating distributions of the second functions versus divisor f values.

* * * * *